United States Patent

Wu

[11] Patent Number: 5,414,178
[45] Date of Patent: May 9, 1995

[54] DIMERIZATION CATALYST SYSTEMS AND PROCESSES

[75] Inventor: An-hsiang Wu, Bartlesville, Okla.

[73] Assignee: Phillips Petroleum Company, Bartlesville, Okla.

[21] Appl. No.: 184,715

[22] Filed: Jan. 21, 1994

Related U.S. Application Data

[62] Division of Ser. No. 915,143, Jul. 17, 1992, Pat. No. 5,320,993.

[51] Int. Cl.$^6$ .................................................. C07C 2/24
[52] U.S. Cl. ................................. 585/513; 585/510; 585/511; 585/512; 585/516
[58] Field of Search ............... 585/510, 511, 512, 513, 585/516

[56] References Cited

U.S. PATENT DOCUMENTS

| | | | |
|---|---|---|---|
| 3,147,240 | 9/1964 | Coover et al. | 502/117 |
| 3,316,229 | 4/1967 | Vandenberg | 502/117 |
| 3,462,406 | 8/1969 | Natta et al. | 502/117 |
| 3,542,899 | 11/1970 | Butte, Jr. | 260/683.15 |
| 3,824,226 | 7/1974 | Gunther et al. | 502/117 |
| 4,659,865 | 4/1987 | Isshiki et al. | 560/232 |

FOREIGN PATENT DOCUMENTS 927532 5/1963 United Kingdom .
1117318 6/1968 United Kingdom .

OTHER PUBLICATIONS

Hata, Go, "A New Catalyst, System for the Dimerization of Ethylene", Chemistry and Industry, Jan. 30, 1965, p. 223.

*Primary Examiner*—Helen M. S. Sneed
*Assistant Examiner*—E. A. Irzinski
*Attorney, Agent, or Firm*—Lynda S. Jolly

[57] ABSTRACT

A catalyst system composition and a process to prepare a catalyst composition comprising a cobalt compound, a metal alkyl and a coordinating compound is provided. The resultant catalyst system composition can be used to dimerize ethylene with high productivity to butenes and high selectivity to 1-butene.

12 Claims, No Drawings

DIMERIZATION CATALYST SYSTEMS AND PROCESSES

This application is a division of application Ser. No. 07/915,143, filed Jul. 17, 1992, and now U.S. Pat. No. 5,320,993, the entirety of which is herein incorporated by reference.

BACKGROUND OF THE INVENTION

This invention relates to ethylene dimerization, dimerization catalyst systems, and processes to prepare dimerization catalyst systems.

A variety of ethylene dimerization catalysts have long been known. Several catalyst compositions, as well as methods of preparing these types of catalysts, are known in the art. The resultant catalyst systems, although useful to dimerize ethylene, do not always have a high conversion rate and/or a high isomer ratio of desired product(s) to undesired product(s). Thus, a dimerization process, because of low conversion and/or low isomer ratio, can be more time consuming and require larger, uneconomical reactor equipment.

SUMMARY OF THE INVENTION

It is an object of this invention to provide an improved catalyst system for the dimerization of ethylene.

It is another object of this invention to provide a method to prepare an improved catalyst system for the dimerization of ethylene.

It is yet a further object of this invention to provide an improved process for the dimerization of ethylene.

In accordance with this invention, a dimerization catalyst system comprising a cobalt compound selected from the group consisting of cobalt enolates, cobalt alkoxides, cobalt carboxylates and mixtures thereof; a metal alkyl compound; and a coordinating compound, which is a nitrogen-containing compound, is provided, In accordance with another embodiment of this invention, processes to prepare novel dimerization catalyst systems are provided.

In accordance with still another embodiment of this invention, these novel catalyst system compositions can be used to dimerize ethylene.

DESCRIPTION OF THE PREFERRED EMBODIMENTS

Catalyst Systems

Catalyst systems prepared in accordance with this invention can be used for ethylene dimerization. Catalyst systems comprise a cobalt compound, a metal alkyl, and a coordinating compound. The cobalt compound can be any cobalt compound selected from the group consisting of cobalt enolates, cobalt alkoxides, cobalt carboxylates, and mixtures thereof. Preferably, the cobalt compound is a cobalt(II) or cobalt(III) compound due to increased reaction rates and productivity. Cobalt(I) compounds are generally very unstable, and therefore, not readily available commercially. Exemplary cobalt compounds include, but are not limited to cobalt hydroxide, cobalt carbonate, cobalt acetylacetenate, cobalt iodide, cobalt acetate, dicobalt octacarbonyl, tetracobalt dodecarbonyl, cobalt hydride tetracarbonyl, dicobalt hexacarbonyl bis-(tri-n-butylphosphine), and mixtures thereof. A cobalt(III) compound is preferred in order to effectuate a more rapid reaction rate and, therefore, higher productivity. Cobalt(II) compounds usually have a slower reaction rate, and therefore, a lower productivity, but a much higher isomer ratio of 1-butene to other butene isomers. Thus, selection of a cobalt compound depends on a choice between productivity and product selectivity.

Suitable cobalt enolates include, but are not limited to, those having a general formula of

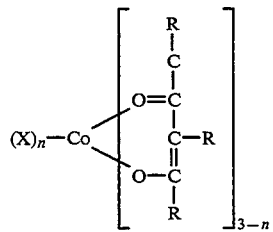

wherein R can be the same or different and R is selected from the group consisting of hydrogen, halides, and aromatic and aliphatic radicals having from about 1 to about 20 carbon atoms per radical and; X is selected from the group consisting of hydrogen, halides, and R; and n is 0, 1 or 2. Preferably, if R is an organic radical, R is an aliphatic radical and has from 1 to 10 carbon atoms per radical, due to commercial availability, ease of use and better reactivity because of decreased steric hindrance. Exemplary preferred cobalt enolates are selected from the group consisting of cobalt acetylacetonate (cobalt 2,4-pentanedionate), cobalt 2,2,6,6-tetramethyl-3,5-heptane-dionate, and mixtures thereof.

Suitable cobalt alkoxides include, but are not limited to having a general formula of

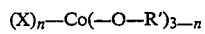

wherein R' can be the same or different and R' is selected from the group consisting of aromatic and aliphatic radicals having from about 1 to about 20 carbon atoms per radical and; X is selected from the group consisting of hydrogen, halides, and R'; and n is 0, 1, or 2. Preferably, R' is an aliphatic radical having from 1 to 10 carbon atoms per radical to commercial availability, ease of use and better reactivity because of decreased steric hindrance. Exemplary preferred cobalt alkoxides are selected from the group consisting of cobalt butoxide, cobalt ethoxide, and mixtures thereof, due to commercial availability and improved catalyst system activity.

Suitable cobalt carboxylates include, but are not limited to cobalt acetate, cobalt 2-ethylhexanoate, cobalt naphthenate, cobalt hexanoate, cobalt octanoate, cobalt decanoate and mixtures thereof. Preferably, the cobalt carboxylate is selected from the group consisting of cobalt 2-ethylhexanoate, cobalt naphthenate, and mixtures thereof due to commercial availability and improved catalyst system activity.

The metal alkyl can have any number of carbon atoms per molecule. However, due to commercial availability and ease of use, the metal alkyl will usually comprise less than about 70 carbon atoms per metal alkyl molecule and preferably, less than about 20 carbon atoms per molecule. Preferred metal alkyls include, but are not limited to, those that have reducing capabilities:, such as, for example, alkylaluminum, alkylboron, alkylmagnesium, alkylzinc, and/or alkyllithium compounds. Exemplary metal alkyls include, but are not limited to, n-butyllithium, s-butyllithium, t-butyllithium, diethylmagnesium, dibutylmagnesium, diethylzinc, triethylaluminum, trimethylaluminum, trisobutylaluminum, and mixtures thereof.

Most preferably, metal alkyls are selected from the group consisting of non-hydrolyzed, i.e., not pre-contacted with water, alkylaluminum compounds, derivatives of alkylaluminum compounds, halogenated alkylaluminum compounds, and mixtures thereof, having the general formulae selected from the group consisting of $AlR_3$, $AlR_2X$, $AlRX_2$, $AlR_2OR$, $AlRXOR$, and/or $Al_2R_3X_3$, wherein R is an alkyl group and X is a halogen atom, for improved product selectivity, as well as improved catalyst system reactivity, activity, and/or productivity. Exemplary alkylaluminum compounds include, but are not limited to, triethylaluminum, tripropylaluminum, tributylaluminum, diethylaluminum chloride, diethylaluminum bromide, diethylaluminum ethoxide, diethylaluminum phenoxide, ethylaluminum chloride, ethylaluminum sesquichloride, and mixtures thereof for best catalyst system activity and product selectivity. The most preferred alkylaluminum compound is triethylaluminum, for best results in catalyst system activity and product selectivity.

The coordinating compound can be any nitrogen-containing compound that can react with a cobalt compound to form a cobalt complex. Broadly, the coordinating compound can be any heteroleptic or homoleptic complex or salt, wherein the organic radical has a lone pair of electrons, provided by a nitrogen atom. While not wishing to be bound by theory, it is believed that the cobalt compound disassociates upon contact with the metal alkyl; then the cobalt coordinates with the coordinating compound.

Exemplary classes of nitrogen-containing compounds include, but are not limited to, pyrrolides, nitriles, amines, and/or amides. Generally, the coordinating compound will have from about 1 to about 20 carbon atoms per radical. Specific exemplary nitrogen-containing compounds include, but are not limited to, nitromethane, dimethylpyrrodine, N,N-dimethylformamide, and N-methylformamide, analine, nitrobenzene, tetramethyldiaminomethane, hexamethyldisilozane, and/or pyrrolidone.

Most preferably, the nitrogen-containing compound is a pyrrolide. As used in this disclosure, a pyrrolide is defined as a compound comprising a 5-membered, nitrogen-containing heterocycle, such as, for example, pyrrole, derivatives of pyrrole, and mixtures thereof. Exemplary pyrrolides are selected from the group consisting of hydrogen pyrrolide (pyrrole), lithium pyrrolide, sodium pyrrolide, potassium pyrrolide, cesium pyrrolide, and/or the salts of substituted pyrrolides, because of high reactivity and activity with the other reactants. Examples of salts of substituted pyrrolides include, but are not limited to sodium 2,5-dimethyl pyrrolide and/or 3,4-dimethyl pyrrolide. When the nitrogen-containing compound is a pyrrolide, the resultant cobalt complex is a cobalt pyrrolide.

The dimerization catalyst system can be prepared according to any method known in the art. Preferably, the cobalt compound, metal alkyl and coordinating compound are combined in a hydrocarbon solvent. Any hydrocarbon solvent can be used, as long as the cobalt compound call dissociate, or at least partially dissolve, in the hydrocarbon solvent. Thus, the hydrocarbon solvent can be any combination of one or more aromatic or aliphatic hydrocarbon compounds. While not wishing to be bound by theory, it is believed that an unsaturated hydrocarbon compound acts as more than a solvent, and can be a reactant and/or a stabilizing component during and/or subsequent to formation of an inventive catalyst system.

Preferred unsaturated hydrocarbon compound solvents include, but are not limited to, unsaturated aliphatic hydrocarbons comprising less than about 70 carbon atoms per molecule, aromatic compounds having from about 6 to about 50 carbon atoms per molecule and most preferably, unsaturated hydrocarbons comprising less than about 20 carbon atoms per molecule, due to commercial availability and ease of use. Specific exemplary unsaturated aliphatic compounds include, but are not limited to, ethylene, 1-hexene, 1,3-butadiene, and mixtures thereof. The most preferred unsaturated aliphatic hydrocarbon solvent is ethylene because ethylene is the dimerization reactant. Specific exemplary unsaturated aromatic hydrocarbon compound solvents include, but are not limited to, toluene, benzene, xylene(o,p,m), mesitylene, cumene, isobutylbenzene, t-butylbenzene, hexamethylbenzene, and mixtures thereof. Most preferably, the unsaturated aromatic hydrocarbon compound solvent is toluene, for ease of use, minimal interference with the resultant catalyst system, and increased dimerization activity.

The catalyst system components can be combined in accordance with any method known in the art. Preferably, the coordinating compound is added to the solvent, and then the cobalt compound can be added to the solution of solvent and coordinating compound. Finally, a metal alkyl can be added to the reaction mixture. Preferably, formation of the catalyst system takes place under an inert atmosphere, in the absence of reducing agents, oxidizing agents, and/or water. Preferably, contacting of catalyst system components occurs in the presence of agitation to thoroughly mix and homogenize the catalyst system. While not wishing to be bound by theory, it is believed that a cobalt ion is formed when the ligand associated with the cobalt component disassociates from the cobalt after the addition of a metal alkyl; then the cobalt ion can coordinate with the coordinating compound. The resultant catalyst system is a homogeneous, i.e. dissolved, catalyst system.

Generally, the molar ratio of elemental cobalt to the metal alkyl is less than about 1:10, preferably within a range of about 1:0.5 to about 1:5. Most preferably, the molar ratio of elemental cobalt to metal alkyl is within a range of 1:2 to 1:4 for best catalyst system productivity. If the molar ratio is too low, productivity of the catalyst system and the quantity of resultant product produced is reduced; molar ratios above those given, catalyst system productivity and product productivity do not seem to increase.

Generally, the catalyst system is prepared in-situ in the reactor, under conditions suitable to form an active catalyst system. Generally, the reaction time to form the catalyst system are times of less than about 24 hours, and preferably times within a range of about 1 second to about 1 hour. Most preferably the catalyst system components are contacted for a time within a range of about 1 second to about 5 minutes prior to use. For ease of operation, reactor temperatures and pressures, as discussed below, are used.

Dimerization Reaction Conditions

Dimerization reaction of the invention can be carried out using either batch or continuous types o:f operation, although catalyst systems of the invention are particularly well suited for continuous operation. When a continuous type of operation is used, new catalyst system needs to be introduced into the dimerization reactor, or dimerization reaction zone. Suitable equipment, such as, for example, autoclaves and tubular reactors are well known in the art and can be employed. No special materials of construction are required, so that steel, stainless steel, and/or glass-lines reactors can be employed.

The reaction temperature can vary depending on the catalyst system in feed(s) employed. Typically, a temperature within a range of about 0° to about 150° C. is suitable. Temperatures of about 25° to about 80° C. are preferred, with the range of 30° to 50° C. most preferred for optimal catalyst system productivity and product selectivity. Too low of a temperature can decrease productivity and too high of a temperature can decrease selectivity. Generally, since the reaction is exothermic, reactor cooling can be employed.

The dimerization reaction can be carried out in a liquid or gas phase by contacting ethylene with a catalyst system, depending on the reaction temperature and pressure employed. Pressure during the dimerization reaction can vary between wide limits. In general, pressures of about 50 to about 2,000 psig are suitable. Preferably, pressures of about 200 to about 1,500 psig are employed, with pressures of about 400 to 900 psig most preferred in order to achieve a good balance between reaction rate and minimized equipment and operating costs necessitated by high reaction pressures. However, pressure is not as critical of a parameter as temperature.

If the reaction is carried out in the liquid phase, solvents or diluents, for the reactants can be used. Suitable unsaturated hydrocarbon solvents were discussed earlier. If the reaction is carried out in the gaseous phase, diluents such as aliphatic hydrocarbons and/or substantially inert gases can be present. Exemplary aliphatic hydrocarbon diluents include, but are not limited to, methane and/or ethane. Exemplary substantially inert gas, diluents include, but are not limited to, nitrogen and/or argon.

The contact time for the dimerization reaction depends on several factors, such as, for example, the activity of the catalyst system, reactor temperature, reactor pressure, reactant concentration, level of conversion desired, as well as several other factors.

The length of time during which the ethylene compounds are contacted with the catalyst system can very conveniently between about 0.1 seconds and about 24 hours, although shorter and longer contact times can be employed. Preferably, times of about 1 minute to about 5 hours are suitable. Most preferably, reaction time within a range of 1 minute to 60 minutes are suitable in order to maximize productivity versus time.

Products

The olefinic products of the invention have established utility in a wide variety of applications, such as, for example, as monomers for use in the preparation of homopolymers, copolymers, terpolymers, e.g. as the third component of ethylene-propylene terpolymers useful as synthetic elastomers, and other polymer applications. The selectivity as a butene isomer product can vary with the amount of coordinating compound used in the catalyst system. Possible butene isomer products include 1-butene, trans-2-butene and cis-2-butene. As the amount of coordinating compound is increased, the selectivity to 1-butene increases and the productivity of the cis- and trans-2-butenes decreases.

A further understanding of the present invention and its advantages will be provided by reference to the following, non-limiting examples.

EXAMPLES

In the following Examples, a 300 316-SS autoclave (from Autoclave Engineers) was used for all reactions. All hydrocarbon solvents were obtained from Fisher Chemicals and distilled over sodium metal/benzophenone prior to use. Triethylaluminum (TEA) and n-butyllithium were obtained from Aldrich Chemicals and were used as received.

Product analysis was performed on a gas chromatograph using a capillary DB-1 (60 m) column. Column conditions were 30° C. hold for 5 minutes, then 15° C./min increase to 285° C. hold for 13 minutes. Hydrocarbons through C-20 were observed to elute under these conditions. Detection was obtained using a flame ionization detector (FID) in the area % mode. An aliquot was taken into a 50 mL pressure sample tube (about 5 g) and analyzed via the application of GC-FID. The selectivity of alpha-olefin and weight percent (wt %) distribution were determined by GC-FID spectra, which were recorded on a Hewlett-Packard HP 5890II GC-FID spectrometer. Productivity was determined by the totalizer readings which were obtained via the application of an ethylene flow meter/totalizer. All branched and isomerized olefins were identified by comparison with commercially available authentic samples.

Example I

Ethylene Dimerization by Using Cobalt(II) Acetylacetonate/Triethylaluminum

A solution of triethylaluminum (TEA) (1.9M, 1.0 ml; 1.9 mmol) was added via syringe to a 40 mL addition vessel. After addition, the addition vessel was immediately sealed and pressured with ethylene to 700 psig. Degassed, freshly distilled toluene (50 mL), pyrrole ($NC_5H_5$) (0–30 molar equivalents of pyrrole to cobalt) and cobalt(II) acetylacetonate (0.244 g; 0.95 mmol) were added to a nitrogen-purged 300 mL autoclave. The system was immediately sealed, purged with ethylene 4 to 6 times and then pressured to 50 psig with ethylene, with agitation (1600 rpm) at ambient temperature for 5 minutes. Ethylene and the solution of TEA, were added to the agitated reactor through an addition valve. Internal ethylene pressure was maintained at 700 psig and temperature was maintained at about 40° C. by using external cooling water for a period of 0.5 to 2 hours. Results are given in Table 1.

A similar procedure was followed for the reaction of cobalt(II) acetylacetonate (0.244 g; 0.95 mmol), triethylaluminum (1.9M; 1.0 mL; 1.90 mmol) and n-butyl chloride (0.30 molar equivalents n-butyl chloride to cobalt). The results are given in Table 2.

TABLE 1[1]

| Ethylene Dimerization Using Cobalt(II)/TEA/Pyrrole | | | | | |
|---|---|---|---|---|---|
| Run | Mol eq. of Pyrrole | Productivity[2] | Wt. % $C_4H_8$ | Wt. % Butene | | |
| | | | | 1- | trans-2- | cis-2- |
| 110 | 0 | 5164 | 99 | 7 | 74 | 19 |
| 111 | 1 | 3951 | 99 | 30 | 50 | 20 |
| 112 | 3 | 2650 | 99 | 46 | 40 | 14 |
| 113 | 5 | 1844 | 99 | 55 | 36 | 9 |
| 114 | 10 | 1183 | 99 | 68 | 24 | 8 |

TABLE 1-continued

Ethylene Dimerization Using Cobalt(II)/TEA/Pyrrole

| Run | Mol eq. of Pyrrole | Productivity[2] | Wt. % C$_4$H$_8$ | Wt. % Butene 1- | trans-2- | cis-2- |
|---|---|---|---|---|---|---|
| 115 | 30 | 1017 | 99 | 81 | 16 | 3 |

[1]Reaction time was 30 minutes; reaction temperature was 40° C.
[2]g oligomers/g cobalt/hour

TABLE 2[1]

Ethylene Dimerization Using Cobalt(II)/TEA/n-Butyl Chloride

| Run | Mol eq. of CH$_3$(CH$_2$)$_3$Cl | Productivity[2] | Wt % C$_4$H$_8$ | Wt. % of Butene 1- | trans-2- | cis-2- |
|---|---|---|---|---|---|---|
| 120 | 0 | 5164 | 99 | 7 | 74 | 19 |
| 121 | 3 | 1848 | 99 | 38 | 48 | 14 |
| 122 | 5 | 1563 | 99 | 49 | 39 | 12 |
| 123 | 10 | 1352 | 99 | 54 | 37 | 9 |
| 124 | 20 | 1294 | 99 | 66 | 26 | 8 |
| 125 | 30 | 1005 | 99 | 71 | 22 | 7 |

[1]Reaction time was 30 minutes; reaction temperature was 40° C.
[2]g oligomers/g cobalt/hour The data in Table 1 for a cobalt(II) compound, show that ethylene can be effectively dimerized to butenes with high catalyst system productivity and high ethylene conversion to butenes. Comparison of Run 110 with Runs 111–115 demonstrates that pyrrole (hydrogen pyrrolide) can effectively increase the selectivity toward 1-butene. The data in Table 1 also show that increasing the molar equivalents of pyrrole used increases the 1-butene product selectivity. Run 120, when compared to Runs 121–125, shows that an alkyl halide can also improve 1-butene product selectivity. However, pyrrole is more effective than an alkyl halide in 1-butene product selectivity, as seen by comparison of Tables 1 and 2.

Example II

A solution of triethylaluminum (TEA) (1.90M; 1.0 mL; 1.90 mmol) was added via syringe to a 40 mL addition vessel. After addition, the addition vessel was immediately sealed, pressured with ethylene to 700 psig. Degassed, freshly distilled toluene (50 mL), pyrrole (NC$_5$H$_4$) (0–300 molar equivalents to pyrrole to cobalt) and cobalt(III) acetylacetonate (0.226 g; 0.635 mmol) were added to a nitrogen-purged 300 mL autoclave. The system was immediately sealed, purged with ethylene 4 to 6 times and then pressured to 50 psig with ethylene, with agitation (1600 rpm) at ambient temperature for 5 minutes. Ethylene and the solution of TEA were added to the agitated reactor through an addition valve. Internal ethylene pressure was maintained at 700 psig and temperature was maintained at about 40° C. by using an external cooling water for a period of 0.5–1 hours. The results are given in Table 3.

A similar procedure also was followed for the reaction of cobalt(III) acetylacetonate (0.244 g; 0.95 mmol), triethylaluminum (1.9M; 1.0 mL; 1.90 mmol) and n-butyl chloride (0–30 molar equivalents of n-butyl chloride to cobalt). The results are given in Table 4.

TABLE 3[1]

Ethylene Dimerization Using Cobalt(III)/TEA/Pyrrole

| Run | Mol eq. of Pyrrole | Rx Temp °C. | Productivity[2] | Wt. % C$_4$H$_8$ | Wt. % Butene 1- | trans-2- | cis-2- |
|---|---|---|---|---|---|---|---|
| 220 | 0 | 42 | 8157 | 99.5 | 4 | 72 | 24 |
| 221 | 1 | 42 | 8449 | 99.4 | 8 | 74 | 18 |
| 222 | 2 | 41 | 8226 | 99.5 | 15 | 60 | 25 |
| 223 | 3 | 40 | 4813 | 99.6 | 23 | 63 | 14 |
| 224 | 5 | 40 | 3541 | 99.5 | 26 | 59 | 15 |
| 225 | 10 | 40 | 2522 | 99.7 | 28 | 58 | 14 |
| 226 | 15 | 40 | 2462 | 99.4 | 32 | 52 | 16 |
| 227 | 30 | 40 | 2185 | 99.6 | 39 | 50 | 11 |
| 228 | 50 | 40 | 1980 | 99.4 | 49 | 39 | 12 |
| 229 | 100 | 40 | 1725 | 99.5 | 61 | 33 | 6 |
| 230 | 300 | 40 | 1589 | 99.5 | 70 | 25 | 5 |

[1]Reaction time was 30 minutes.
[2]g oligomers/g cobalt/hour

TABLE 4[1]

Ethylene Dimerization Using Cobalt(III)/TEA/n-Butyl Chloride

| Run | Mol eq. of CH$_3$(CH$_2$)$_3$Cl | Productivity[2] | Wt % C$_4$H$_8$ | Wt. % of Butene 1- | trans-2- | cis-2- |
|---|---|---|---|---|---|---|
| 231 | 0 | 8157 | 99 | 4 | 72 | 24 |
| 232 | 3 | 2694 | 99 | 31 | 52 | 17 |
| 233 | 5 | 2235 | 99 | 43 | 43 | 14 |
| 234 | 10 | 1864 | 99 | 52 | 36 | 12 |
| 235 | 20 | 1532 | 99 | 61 | 30 | 9 |
| 236 | 30 | 1468 | 99 | 69 | 24 | 7 |

[1]Reaction time was 30 minutes; reaction temperature was 40° C., except Run 231 which was 42° C.
[2]g oligomers/g cobalt/hour The data in Tables 3 and 4, for a cobalt(III) compound, also show that ethylene can be effectively dimerized to butenes with high catalyst system productivity and high ethylene conversion to butenes. Comparison of Runs 220 and 231 with all other Runs shows that a coordinating compound (ligand) can increase butene isomer selectivity to 1-butene.

Comparison of the data in Tables 1 and 2 with the data in Tables 3 and 4 demonstrates that cobalt(II) compounds are more effective dimerization catalyst system components than cobalt(III) compounds, when 1-butene is the desired isomer product, in that Tables 1 and 2 show a higher selectivity to 1-butene when the same molar equivalents of coordinating compound is used. Conversely, productivity for cobalt(III) compounds is much higher than productivity for cobalt(II) compounds. Hence, choice of the cobalt compound depends on the desired result; cobalt(II) is used to enhance selectivity, i.e., isomer ratio, and cobalt(III) is used to enhance productivity.

While this invention has been described in detail for the purpose of illustration, it is not to be construed as limited thereby but is intended to cover all changes and modifications within the spirit and scope thereof.

That which is claimed is:

1. A process to dimerize ethylene under conditions to effect dimerization by contacting ethylene with a catalyst system composition comprising:
    (a) a cobalt compound selected from the group consisting of cobalt enolates, cobalt alkoxides, cobalt carboxylates, and mixtures thereof;
    (b) a metal alkyl wherein said metal is selected from the group consisting of aluminum, boron, zinc, magnesium, lithium, and mixtures thereof; and
    (c) a coordinating compound which is a nitrogen-containing compound selected from the group consisting of pyrrole (hydrogen pyrrolide), alkali metal salts of pyrrole, alkali metal salts of pyrrolides, and mixtures thereof.

2. A process according to claim 1 wherein said cobalt compound is selected from cobalt(II) compounds, cobalt(III) compounds, and mixtures thereof.

3. A process according to claim 2 wherein said cobalt compound is a cobalt(III) compound.

4. A process according to claim 1 wherein said metal alkyl is an aluminum alkyl.

5. A process according to claim 4 wherein said aluminum alkyl is triethylaluminum.

6. A process according to claim 1 wherein said coordinating compound is pyrrole (hydrogen pyrrolide).

7. A process according to claim 1 wherein the molar ratio between said cobalt compound and said metal alkyl is less than about 1:10.

8. A composition according to claim 1 wherein the molar ratio of said coordinating compound to cobalt compound is less than about 400:1.

9. A process according to claim 1 wherein said ethylene dimerization process occurs at a temperature within a range of about 0° to about 100° C., a pressure within a range of about 50 to about 2,000 psig, and a time within a range of about 0.1 seconds to about 24 hours.

10. A process to dimerize ethylene under conditions to effect dimerization by contacting ethylene with catalyst system composition prepared by a process comprising contacting a cobalt compound selected from the group consisting of cobalt enolates, cobalt alkoxides, cobalt carboxylates, and mixtures thereof; a metal alkyl wherein said metal is selected from the group consisting of aluminum, boron, zinc, magnesium, lithium, and mixtures thereof; and a coordinating compound which is a nitrogen-containing compound selected from the group consisting of pyrrole (hydrogen pyrrolide), alkali metal salts of pyrrole, alkali metal salts of pyrrolides, and mixtures thereof, in the presence of a hydrocarbon solvent;

wherein said dimerization process occurs under an inert atmosphere, at a temperature within a range of about 0° to about 150° C., and at a pressure within a range of about 50 to about 2,000 psig.

11. A process to dimerize ethylene under conditions to effect dimerization by contacting ethylene with a catalyst system composition comprising;

(a) cobalt(III) acetylacetonate;
(b) triethylaluminum; and
(c) pyrrole (hydrogen pyrrolide).

12. A process according to claim 11 wherein said dimerization process occurs at a temperature within a range of about 0° to about 100° C. and a pressure within a range of about 50 to about 2,000 psig.

* * * * *